(12) United States Patent
Luup

(10) Patent No.: US 10,311,562 B2
(45) Date of Patent: Jun. 4, 2019

(54) IMAGING SYSTEM FOR GRANULAR MATERIAL WITH HOMOGENEOUS BACKGROUND

(71) Applicant: CGRAIN AB, Uppsala (SE)

(72) Inventor: Jaan Luup, Uppsala (SE)

(73) Assignee: CGRAIN AB, Uppsala (SE)

( * ) Notice: Subject to any disclaimer, the term of this patent is extended or adjusted under 35 U.S.C. 154(b) by 0 days.

(21) Appl. No.: 15/302,637

(22) PCT Filed: Mar. 30, 2015

(86) PCT No.: PCT/SE2015/050379
§ 371 (c)(1),
(2) Date: Oct. 7, 2016

(87) PCT Pub. No.: WO2015/156722
PCT Pub. Date: Oct. 15, 2015

(65) Prior Publication Data
US 2017/0032516 A1 Feb. 2, 2017

(30) Foreign Application Priority Data
Apr. 7, 2014 (SE) ...................................... 1450426

(51) Int. Cl.
G06K 9/00 (2006.01)
G06T 7/00 (2017.01)
(Continued)

(52) U.S. Cl.
CPC .............. G06T 7/0004 (2013.01); B07C 5/34 (2013.01); B07C 5/3425 (2013.01); G01B 11/00 (2013.01);
(Continued)

(58) Field of Classification Search
CPC ........... G06K 7/10; G06K 2007/10485; G06K 9/00127; G06K 9/20; G06K 9/2009;
(Continued)

(56) References Cited

U.S. PATENT DOCUMENTS 4,025,201 A * 5/1977 Deane ................ G01N 21/9036
356/239.4
4,351,437 A * 9/1982 Long ...................... A01D 33/04
356/634

(Continued)

FOREIGN PATENT DOCUMENTS

CN 1356492 7/2002
CN 1715890 1/2006
(Continued)

OTHER PUBLICATIONS

Supplementary European Search Report dated Jan. 24, 2018 in corresponding European Patent Application No. 15776846.
(Continued)

Primary Examiner — Eric Rush
(74) Attorney, Agent, or Firm — Young & Thompson

(57) ABSTRACT

An imaging system (100) including at least one camera (3), a background element (4) and a pair of mirrors (2a, 2b), where the mirror surfaces of the mirrors in the pair are angled from each other at an angle α, where the imaging system (100) is intended to receive a sample along a main axis extending between the mirrors. The camera (3) is directed towards the mirror pair (2a, 2b) and the background element (4) includes a surface directed towards the mirror pair, where the background element (4) is formed as a cylinder portion with a cylinder axis deviating from the main axis, and the mirrors are arranged with a respective mirror surface edge to edge with each other.

7 Claims, 6 Drawing Sheets

(51) Int. Cl.
  *G01N 15/14* (2006.01)
  *G06K 9/20* (2006.01)
  *G01N 21/95* (2006.01)
  *B07C 5/34* (2006.01)
  *B07C 5/342* (2006.01)
  *G01B 11/00* (2006.01)
  *G01N 21/85* (2006.01)
  *G01N 21/88* (2006.01)
  *G06K 7/10* (2006.01)

(52) U.S. Cl.
  CPC ....... *G01N 15/147* (2013.01); *G01N 15/1475* (2013.01); *G01N 21/85* (2013.01); *G01N 21/88* (2013.01); *G01N 21/9508* (2013.01); *G06K 9/00127* (2013.01); *G06K 9/20* (2013.01); *G06K 9/2009* (2013.01); *G06K 9/209* (2013.01); *B07C 2501/009* (2013.01); *G01N 2021/8592* (2013.01); *G01N 2201/062* (2013.01); *G01N 2201/0636* (2013.01); *G06K 2007/10485* (2013.01); *G06T 2207/30128* (2013.01)

(58) Field of Classification Search
  CPC .. G06K 9/209; G01N 15/147; G01N 15/1475; G01N 21/85; G01N 21/8901; G01N 21/8914; G01N 21/9508; G01N 2021/8832; G01N 2021/8592; G01N 21/88; G01N 2201/062; G01N 2201/0636; G06T 7/0004; G06T 2207/30128; B07C 5/34; B07C 5/3425; B07C 2501/009; G01B 11/00
  USPC ........ 382/100, 108–110, 141–143, 152, 312, 382/321–325; 356/237.1, 237.2, 238.1, 356/239.1, 335; 250/559.07, 559.08
  See application file for complete search history.

(56) References Cited

U.S. PATENT DOCUMENTS

| | | | | |
|---|---|---|---|---|
| 5,175,428 A | * | 12/1992 | Agerskov | G01N 21/9054 250/223 B |
| 5,243,402 A | * | 9/1993 | Weber | G01N 21/8901 250/559.15 |
| 5,424,838 A | * | 6/1995 | Siu | G01N 21/95684 356/237.1 |
| 5,448,365 A | | 9/1995 | Grollimund et al. | |
| 5,621,530 A | | 4/1997 | Marrable, Jr. | |
| 5,936,725 A | * | 8/1999 | Pike | G01N 21/952 348/125 |
| 6,516,083 B1 | * | 2/2003 | Bonechi | G01N 21/952 382/141 |
| 7,782,451 B2 | | 8/2010 | Matsumoto et al. | |
| 8,208,016 B2 | | 6/2012 | Maurin | |
| 2002/0064043 A1 | | 5/2002 | Ariga et al. | |
| 2006/0152741 A1 | | 7/2006 | Quist | |
| 2007/0121107 A1 | * | 5/2007 | Tsai | G01N 21/8806 356/237.2 |
| 2007/0211240 A1 | | 9/2007 | Matsumoto et al. | |
| 2008/0074648 A1 | * | 3/2008 | Lampalzer | G01B 11/24 356/73 |
| 2009/0002694 A1 | * | 1/2009 | Paavola | G01N 21/8806 356/237.2 |
| 2010/0118134 A1 | | 5/2010 | Maurin | |
| 2012/0092859 A1 | * | 4/2012 | Gregoris | G03B 15/03 362/217.06 |
| 2014/0241590 A1 | * | 8/2014 | Day, Jr. | G06T 7/62 382/110 |
| 2015/0115036 A1 | * | 4/2015 | Ben-Shalom | G06K 7/10742 235/462.42 |
| 2015/0375270 A1 | * | 12/2015 | Ishizu | G01N 21/85 209/580 |

FOREIGN PATENT DOCUMENTS

| | | | | |
|---|---|---|---|---|
| CN | 101034070 | | 9/2007 | |
| EP | 0639764 | | 2/1995 | |
| EP | 0937978 | | 8/1999 | |
| EP | 0 968 772 A2 | | 1/2000 | |
| EP | 1464949 | | 10/2004 | |
| FR | 2914423 | | 10/2008 | |
| JP | 8-5563 A | | 1/1996 | |
| JP | 9-304294 A | | 11/1997 | |
| JP | 2005172608 | | 6/2005 | |
| JP | 2005172608 A | * | 6/2005 | ......... G01N 21/9508 |
| JP | 2009128158 | | 6/2009 | |
| WO | 2005/111538 A1 | | 11/2005 | |

OTHER PUBLICATIONS

International Search Report, dated Jun. 8, 2015, from corresponding PCT Application.
Chinese Office Action dated Jul. 18, 2018 in corresponding Chinese Patent Application No. 201580030322.3 with English translation of Chinese Office Action.

* cited by examiner

IMAGING SYSTEM FOR GRANULAR MATERIAL WITH HOMOGENEOUS BACKGROUND

BACKGROUND

Technical Field

The present invention generally relates to imaging of granular material, particularly relating to an imaging system for use in imaging and analysis of e.g. grain.

Background

Imaging systems are often used for determining, with digital image processing, if a product fulfils desired appearance requirements, to thereby register or eliminate products that are faulty in shape and colour, or damaged products. E.g. seeds, grains of salt, berries, tablets or other samples are inspected through such imaging systems and a connected subsequent image processing system can thereafter analyse the sample in real time and determine if the sample is faulty and should be removed or registered. Imaging systems do not have to be used for only detecting and discarding faulty or defective samples, but can also be used for determining quality of samples and collecting statistics for future evaluation of the sample. For best results the sample should be imaged around its entire periphery and a way to do this is with a V-shaped angled pair of mirrors between which the samples flow, as for example in US2006152741.

To facilitate the image processing by creating a homogeneous background against which the sample is clearly distinguished, the system is often provided with a background element such as in US2006152741. This is however not enough for obtaining several separate images of the sample against a completely homogeneous background, which is desirable. With a system arranged as in US2006152741 reflected light will furthermore reach the camera, which is added to the image and makes it more difficult for the image processing system to distinguish faults in the samples from disturbing stray light and inhomogeneity in the background of the image, not related to the sample. One of the problems with an inhomogeneous background is that it obstructs a subsequent analysis of the images. Inhomogeneous elements in the background may affect and disrupt an automated digital image processing and obstruct the analysis of the actual sample.

There is thus a need for imaging systems that overcome one or more of the problems mentioned above.

SUMMARY OF THE INVENTION

The invention relates to an imaging system comprising at least a camera, a background element and a pair of mirrors. The mirror surfaces of the mirrors in the pair are located against each other along an edge and are angled from each other in an angle α. The imaging system is intended to receive a sample along a main axis extending between the mirrors, such that the mirror pair favourably generates three images of the sample seen from three different angles of sight. The camera is directed towards the mirror pair and the background element comprises a curved surface which is directed towards the mirror pair and creates a background to the images that facilitates image processing.

In an advantageous embodiment of the invention a division plane extends through the mirror pair, substantially perpendicular to the main axis. The main part of the camera is arranged on a first side of the division plane and at least part of the background element is arranged on a second side of the division plane. Thereby, the camera does not end up within its own field of view.

In a further embodiment of the invention the surface of the background element that is directed towards the mirror pair is illuminated by at least one background illumination element which is directed towards this surface. With the background illumination element directed in this way, no direct light from this ends up in the field of view of the camera. Typically the background illumination elements are arranged close to the outer edge of the background element, so that the illumination elements themselves also do not end up in the field of view of the camera.

In a further embodiment the imaging system is intended to receive samples with a typical colour and the background element presents a surface directed towards the mirror pair having a colour which is substantially complementary to the typical colour of the sample. As an example, the imaging system may be intended to receive seeds and the background element is then with particular advantage blue.

One of the advantages of the present invention is that it will be possible to image objects using several images and achieve a more homogeneous background than prior art.

DETAILED DESCRIPTION

A purpose of the present invention is to provide an imaging system that produces multiple images of a sample against a significantly more homogeneous background than what has been possible with prior art. The present invention will be described mainly when used for imaging and analysis of grain such as e.g. corn and seeds, but it is also possible to use when analysing other granular objects or foodstuffs, e.g. fruit, gravel, pellets etc. These and other purposes are achieved by an imaging system according to the characterizing parts of the independent claim.

In the description of the figures below reference is made to a main axis (V) and a division plane (D). The main axis is defined by the line along which a sample, typically a seed, is moving through the imaging system. A simple and practical way to arrange the imaging system is of course so that the sample falls by its own weight straight down and in such a case the here denoted main axis consists of an actual vertical axis, but it is of course also possible to let the sample fall slightly obliquely relative to the actual vertical axis with the aid of some kind of guiding pipe or by throwing the sample through the imaging system. In the description it is assumed for simplicity that the main axis corresponds to an axis with vertical extension so that simple terms such as up and down can be used.

The division plane cuts through the system and has an extension typically perpendicular to the main axis. For the common case where the main axis is vertical, the division plane typically consists of a horizontal plane. It should however be understood that the division plane can describe an extension which is arranged in another way than perpendicular to the main axis.

Figure 1:
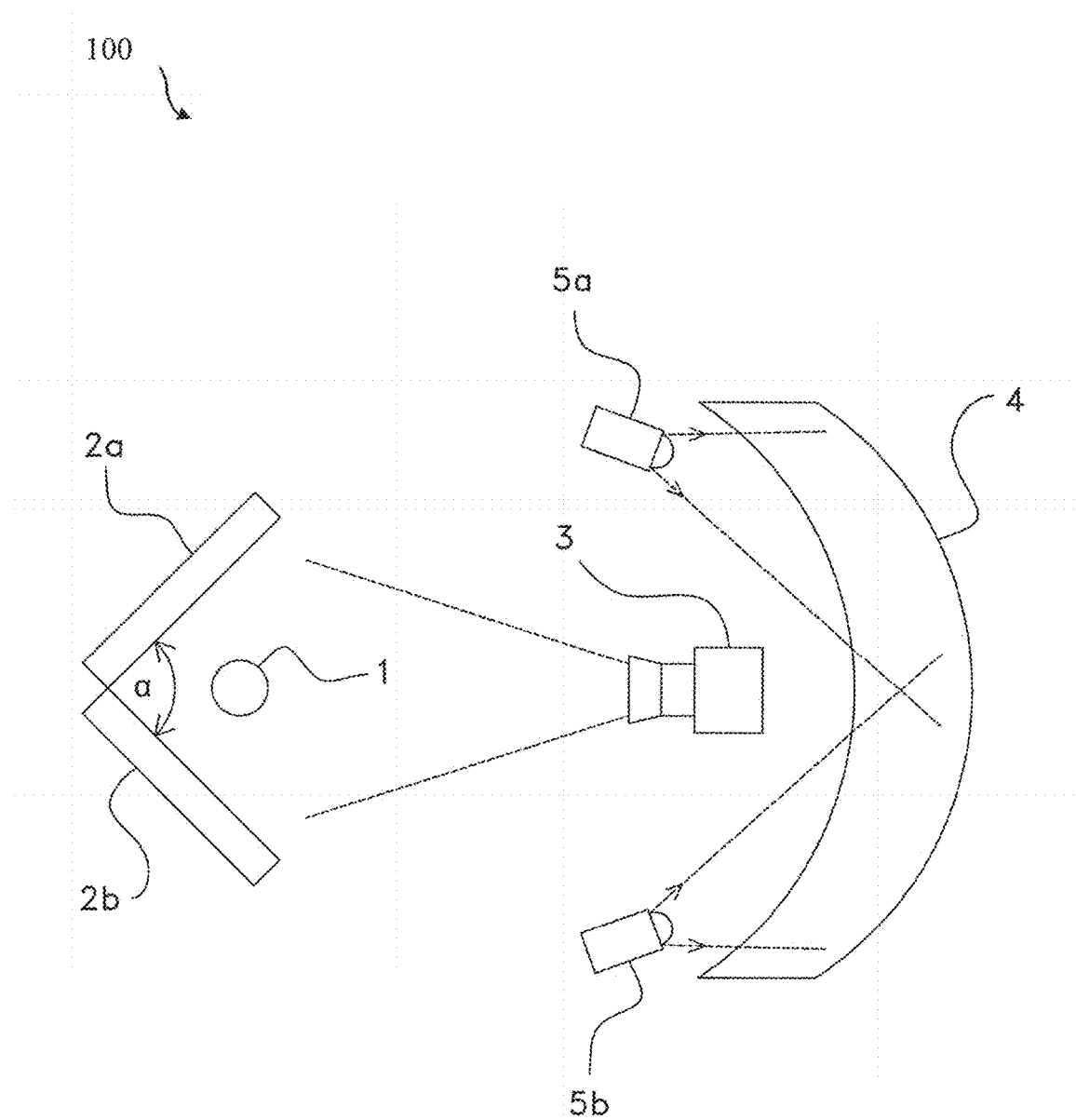
FIG. 1 schematically shows a first embodiment of the invention seen from above.

FIG. 1 schematically shows a first embodiment of an imaging system 100 according to the invention where this is viewed from above, i.e. along the previously described main axis (V). The figure illustrates a sample 1, here in the form of a seed falling down through the imaging system between two mirrors 2a, 2b. The mirrors have a respective rectangular mirror surface and are arranged with a respective mirror surface edge to edge with each other. The mirrors are angled from each other with an angle α, which in this embodiment is a right angle. Thereby the two mirrors 2a, 2b form a substantially v-shaped mirror.

A camera 3 is directed towards the main axis and the seed falling along the main axis, so that a first direct image of the seed appears in the camera. Since the mirrors according to a first embodiment are angled 45 degrees from the line between the camera and the main axis, the seed is imaged through a first mirror 2a in a second image from the side in the camera and through a second mirror 2b in a third image in the camera. In the camera 3 the seed is thus imaged seen from three different angles chosen so that the seed is imaged along its entire circumference in a single image.

Figure 2:
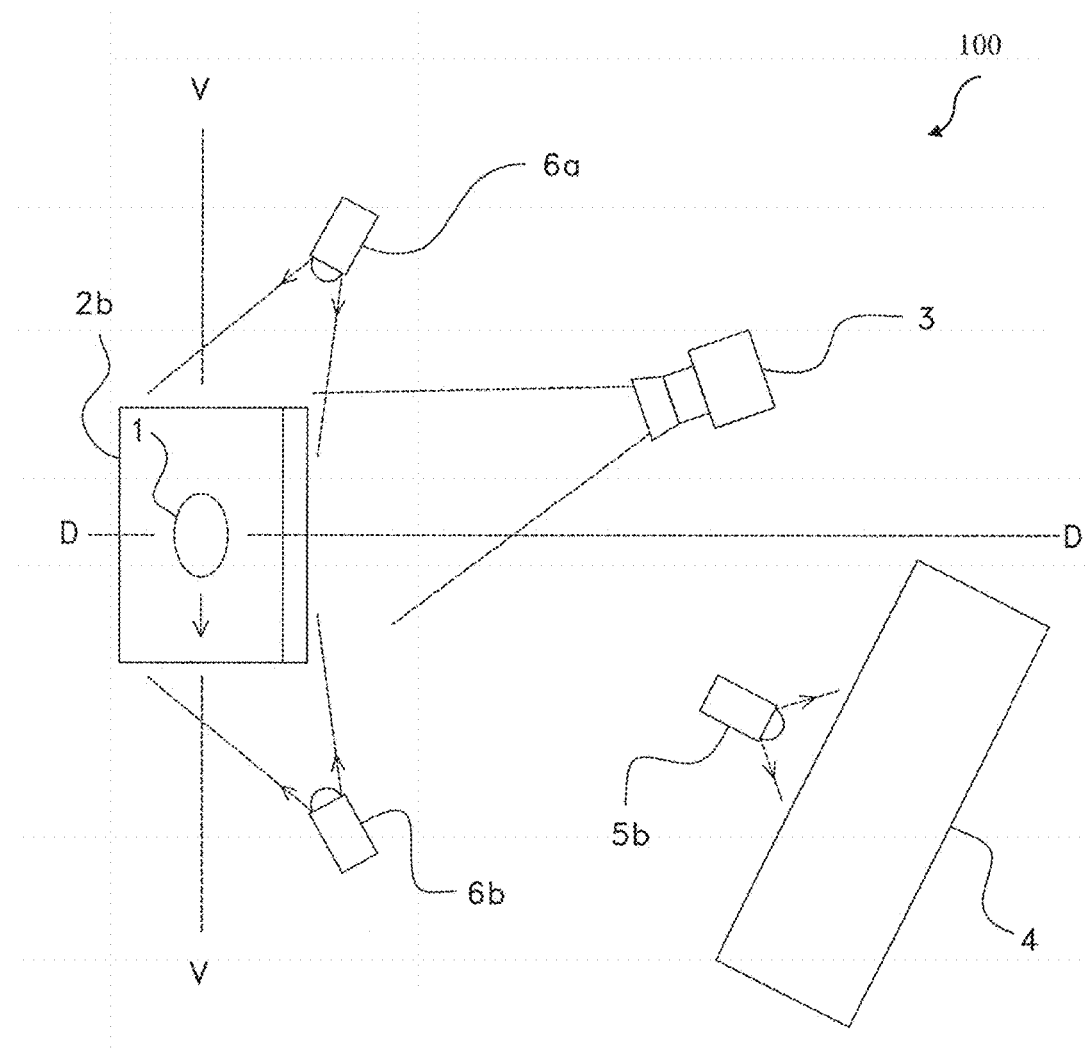
FIG. 2 schematically shows the first embodiment of the invention seen from the side.

In all three images of the seed from three different angles, the camera sees through reflection in both mirrors a background element or background surface 4. In the figure the background element 4 is depicted as if it were located beyond the camera to simplify the illustration, but in fact it does not need to but may according to a further embodiment instead be located below the camera as illustrated in FIG. 2. The background element 4 has an extension such that it covers the entire field of view of the camera 3, as this extends through double reflections in the mirror pair. In a typical application the sample is a seed, which is often yellowish white of yellowish and the properties of the background element 4 is advantageously chosen in a complementary colour, which in this case preferably is blue, to obtain the best possible contrast. For other colours of the sample to be analysed the complementary colour that best enhances the contrast between the sample and the imaged background surface 4 is chosen.

The background element 4 is illuminated with background illumination elements 5a, 5b, that also are directed so that the camera 3 is not affected by specular reflections in the background 4 from the light from the background illumination elements 5a, 5b, which is more clearly illustrated in FIG. 2.

According to a further embodiment the background element 4 may be designed so that it presents properties which, at imaging of samples and background element 4, allow for possibilities for further analysis of the sample in subsequent image processing.

The background illumination elements 5a, 5b are arranged in connection with the right and the left side of the background, respectively, and directed towards the middle of the background, so that both of them are located outside of the field of view of the camera. They may however be arranged in another manner to provide illumination of the background.

The background element 4 is according to this embodiment formed as a cylinder portion with a cylinder axis deviating from the main axis. The cylinder portion forms an arc, the inside of which faces the main axis so that it is approximately directed towards the main axis over its entire surface to achieve the smoothest brightness possible over the entire surface of the image in all three images of the seed. The background illumination elements 5a, 5b are also illuminating, partly overlapping, different parts of the background so that it is as evenly illuminated as possible for the same purpose. Thereby the background element 4 constitutes a substantially concave reflecting surface for incident illumination.

FIG. 2 schematically shows the first embodiment of the imaging system 100 according to the invention seen from the side. Here the main axis V is illustrated as a dashed line extending through the center of the seed 1. The direction of motion of the seed is also illustrated for clarity with an arrow directed downwards in the figure. Since the seed is located between the mirrors in the mirror pair 2a, 2b, it is thus illustrated in a partial cross-section and is therefore depicted with dashed lines.

The division plane D extends perpendicularly to the plane of the paper along a line from right to left and cuts straight through the position of the seed as this is placed in the figure. The camera 3 is arranged above this imaginary division plane D and is directed obliquely downwards towards the position of the seed. The background element 4 is for clarity reasons arranged in its entirety below the division plane D, so that what the camera sees, apart from the seed, only consists of the background element 4. Seen from this perspective the background illumination elements 5b appear to be located in the field of view of the camera, but as is apparent from FIG. 1 they are located respectively on this side and beyond the paper plane of the figure, and thus outside of the field of view of the camera.

In the figure two sample illumination elements 6a, 6b are also illustrated, which are arranged respectively obliquely above and obliquely below the sample 1 and the mirror pair 2a, 2b. They are displaced from the main axis V towards the camera 3 and the background element 4 so as to not be located in the way of the falling seed 1, and directed towards the seed 1 in such a way that the light passing the seed 1 does not hit the camera 3, neither directly nor via the background. The part of this light that falls outside of the mirror pair 2a, 2b may suitably be absorbed by a first, not illustrated, dark light trap, and the part that after double reflection in the mirror pair 2a, 2b is directed approximately towards an opposite sample illumination element is suitably absorbed by a second, not illustrated, dark light trap.

In the illustrated embodiment both mirrors in the mirror pair 2a, 2b respectively have a normal in a plane perpendicular to the main axis. This is of course not entirely necessary and applications could be possible where a deviation from this alignment would be suitable, but typically this is optimal. In the illustrated embodiment the camera in its entirety is arranged above the division plane and the background in its entirety is arranged below the division plane D, but in general this is not necessary and the virtual division plane is just intended to support the explanation of the positioning of the components. If the background element 4 is located beyond the camera, as shown here, there is of course nothing that prevents it from extending further above the division plane behind the camera 3 and this then allows the camera 3 to be moved from its illustrated position or re-directed if needed, with part of the background element 4 maintained as a background in the image of the seed. One of the reasons for positioning the camera 3 above the division plane D is that no part of the camera 3 itself is reproduced in the image from the camera 3, but this is also not strictly necessary but only suitable and advantageous to facilitate subsequent image analysis, where three completely separate images of the seed seen from three different angles against a background which in its entirety is homogeneous and in a complementary colour are reproduced in the image from the camera. The image that is reproduced by the camera thus facilitates future image analysis since it has a background that is as homogeneous as possible, without disturbing elements other than the sample itself.

Figure 3:
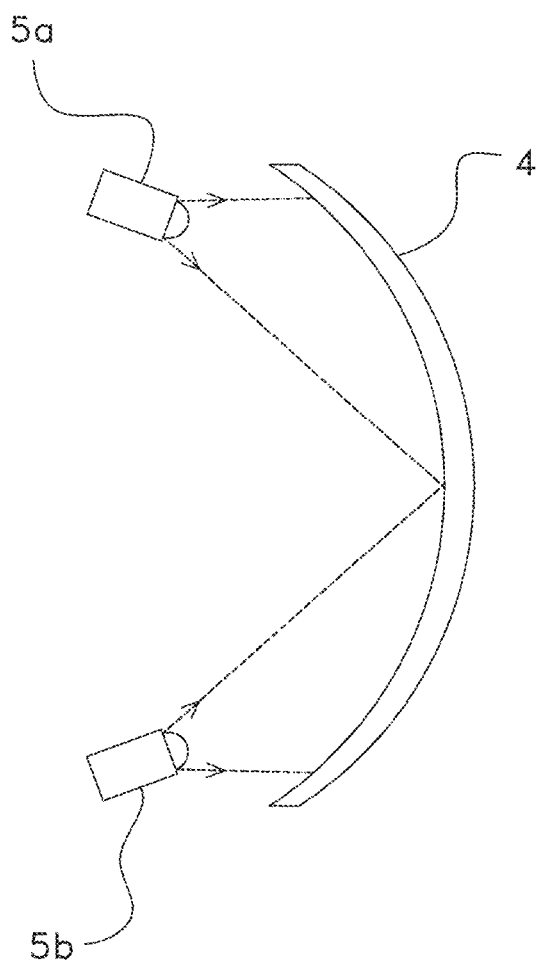
FIG. 3 schematically shows a background element viewed from its upper edge.

FIG. 3 schematically shows a background element 4 seen from its upper edge, i.e. from a view that is not parallel to the main axis since the background is angled from the main axis. The background element 4 is illustrated from this perspective as a circular segment with a certain width. In connection with the upper edge, as seen in the figure, of the background element 4 there is a first background illumination element 5a directing light mainly towards the upper part of the background element, and in connection with the lower edge of the background element there is a second background illumination element 5b directing light mainly towards the lower part of the background element. Part of the light from the two background illumination elements 5a, 5b will be reflected specularly and to a large extent this reflection will fall on the part of the background element 4 not directly illuminated by a respective background illumination element 5a, 5b. In this manner the light from the background illumination elements 5a, 5b are utilized efficiently and are distributed in a more homogeneous manner than if only direct incident light had been utilized.

Figure 4:
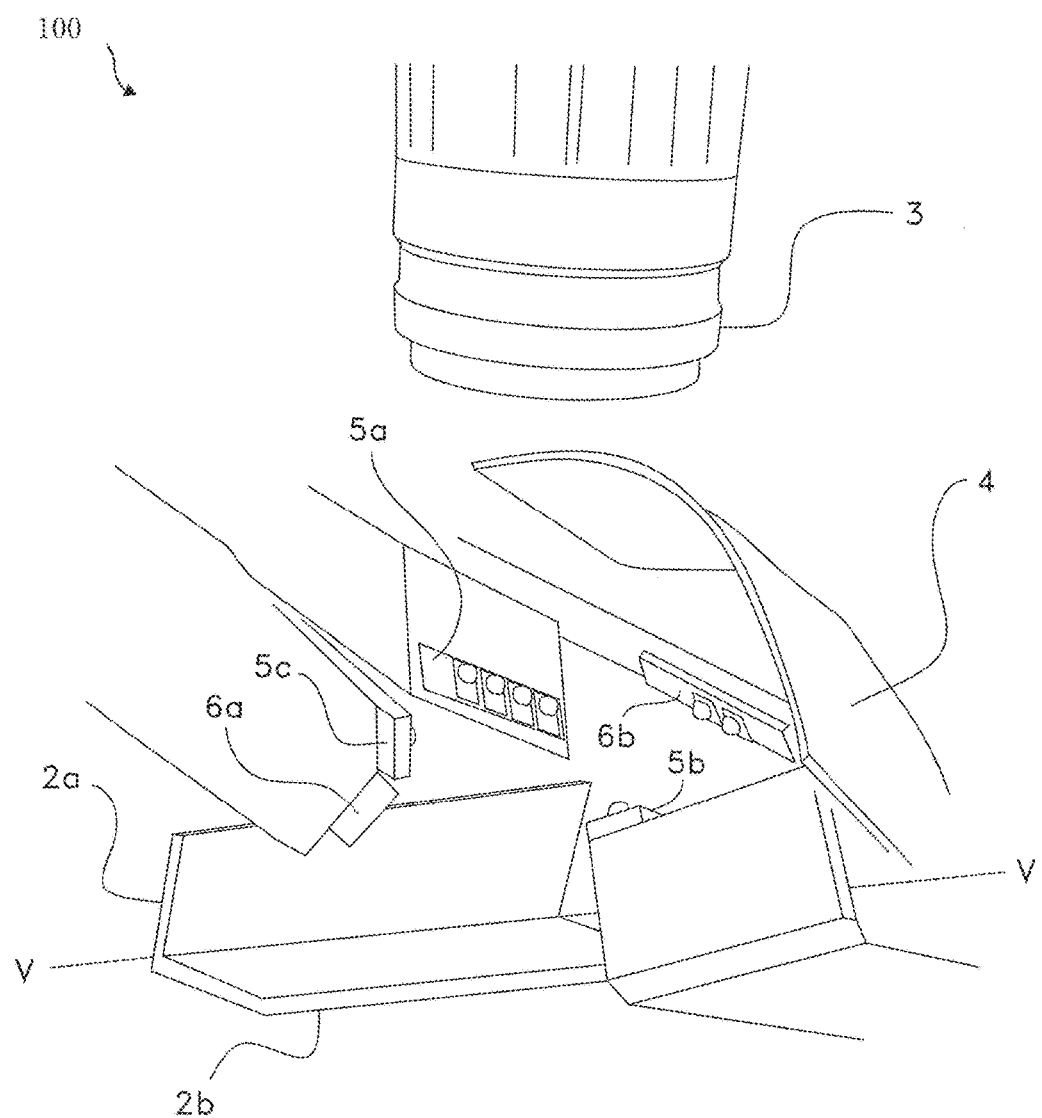
FIG. 4 shows a second embodiment of the invention from a first perspective.

FIG. 4 shows a second embodiment of an imaging system 100 according to the invention from a first perspective. In the figure the main axis V is illustrated to facilitate the understanding. The camera 3 is directed towards the mirror pair 2a, 2b. The background element 4 is in this embodiment arranged not farther away from the mirror pair 2a, 2b than the front surface of the camera 3 and is located below the division plane. The seed, not illustrated here, is illuminated obliquely from below by a lower sample illumination element 6b and obliquely from above by an upper sample illumination element 6a. Each illumination element consists here of groups of LEDs arranged in rows, which LEDs can produce a diffuse light with a wide opening angle. LEDs also have the advantage that they are efficient and can yield light only in a desired wave length region, and they can also quickly be turned off and on to generate illumination only when the seed is located in the correct position between the mirror pair 2a, 2b.

The background element 4 bends also in this embodiment in an arc forming part of a cylinder surface. The background element 4 is here illuminated from both sides in the same manner as in the first embodiment with first and second background illumination elements 5a, 5b, but the imaging system here also comprises a third background illumination element 5c illuminating the background element 4 obliquely from above, i.e. the above seen from the perspective of the axis of the cylinder surface. This third background illumination element 5c is thus arranged relative to the background element in a manner corresponding to the position and direction of the sample illumination elements 6a, 6b relative to the mirror pair.

Figure 5:
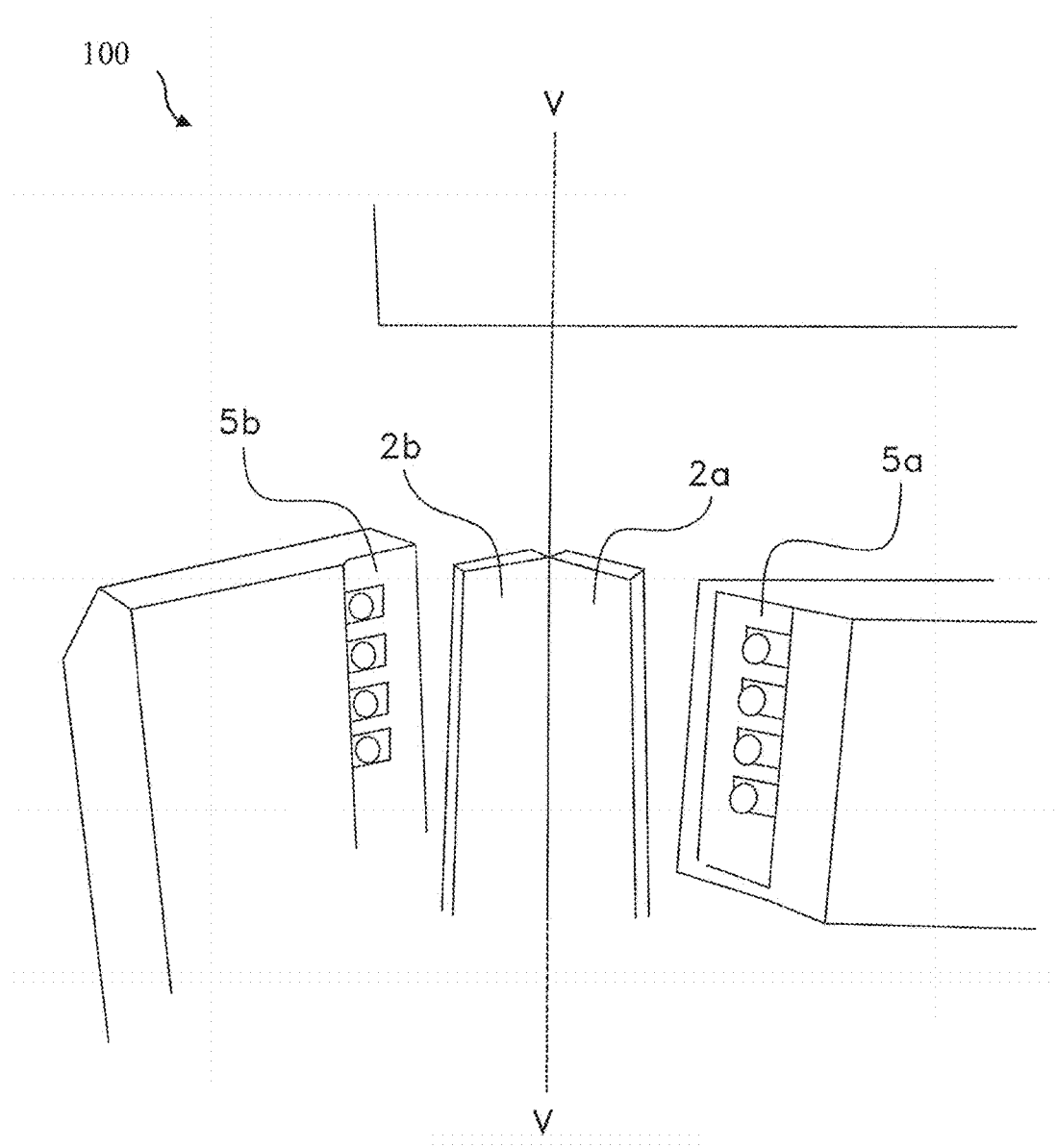
FIG. 5 shows parts of the second embodiment of the invention from a second perspective.

FIG. 5 shows parts of the second embodiment of the imaging system 100 according to the invention from a second perspective, where the main axis V extends from top to bottom. In the figure the mirror pair 2a, 2b and the first and second background illumination elements 5a, 5b are illustrated, while the background element and camera are not visible. Seeds falling down from a, not illustrated, chute fall further downwards in the interior of the mirror pair.

In the embodiments above a camera is described, but this concept here refers to any imaging device, CCD cameras or otherwise. The mirrors in the mirror pair are here rectangular and angled 90° from each other, but the mirrors can of course be differently shaped and angled from each other in another angle than 90°.

Figure 6:
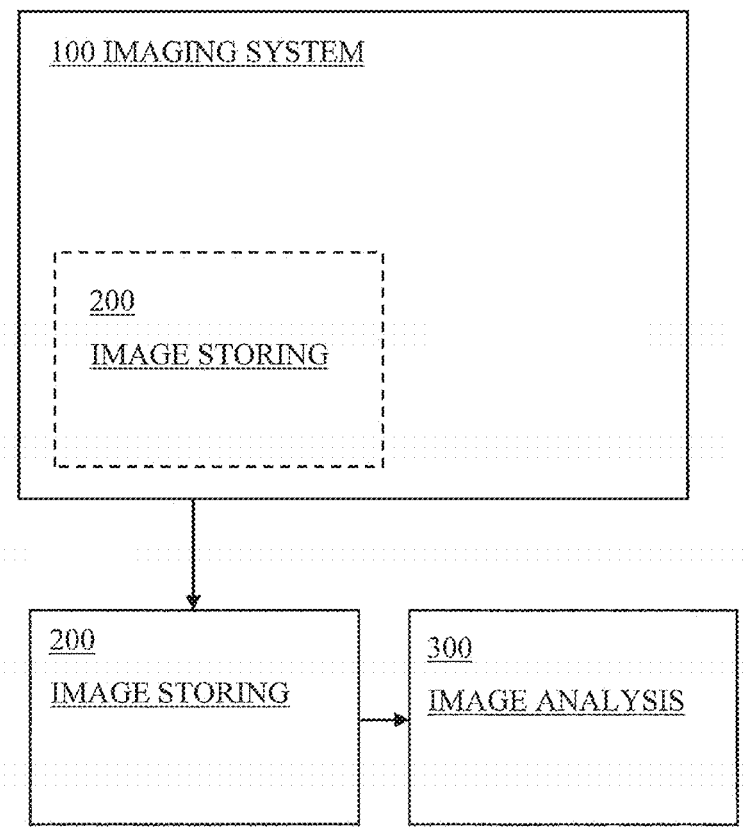
FIG. 6 shows a further embodiment of an imaging system according to the invention.

The imaging system 100 according to the above is arranged for generating images and making them available for storing and analysis in connected storing and image analysis equipment, see FIG. 6. This can be achieved by storing images in a memory 200 in the camera and thereafter transferring these to an image processing system 300. Alternatively the camera may be connected to an external storage medium 200 where the images are stored and then transferred to image analysis equipment 300 for further analysis. According to a further embodiment the camera may be directly connected to an image analysis system 300 where the images are automatically and continuously analysed as long as any sample is present between the pair of mirrors. Additionally, the imaging system 100 may be connected to a control system which makes it possible to control the imaging system based on the outcome of the subsequent image analysis, e.g. by adapting the type of images that are collected based on what is detected at the analysis.

According to the description above the colour of the background element 4 can be chosen as a complementary colour of the sample that is to be imaged.

Depending of the type of camera 3 used, the imaging properties of the background element 4 can be chosen to enhance the contrast between the imaged object and the imaged background. Thereby the term colour can be used also to indicate that the background element 4 has been given a predetermined pattern or other imaging property that will affect a subsequent analysis.

With the aid of the above described embodiments of an imaging system 100 it is possible to image one and the same sample from several different sides and against a homogeneous background which simplifies a subsequent analysis and image processing.

The above described embodiments only serve as examples, and it should be understood that the described technology is not limited thereto. The skilled person understands that various modifications, combinations and changes can be made of the embodiments without diverting from the scope that is defined by the attached claims. In particular, different part solutions of the different embodiments can be combined into other configurations where technically possible.

The invention claimed is:

1. An imaging system (100) comprising:
at least one camera (3),
a pair of mirrors (2a, 2b),
wherein the at least one camera (3) is directed towards the pair of mirrors (2a, 2b),
wherein respective mirror surfaces of the mirrors in the pair of mirrors (2a, 2b) are angled from each other at an angle α and the mirrors (2a, 2b) are arranged with the respective mirror surfaces edge to edge with each other,
wherein the imaging system (100) is intended for receiving a sample along a main axis (V) extending between the pair of mirrors, and
a background element (4) formed as a cylinder portion with a cylinder axis deviating from the main axis,
wherein said background element (4) comprises a surface directed towards the pair of mirrors (2a, 2b) and is placed within a field of view of the at least one camera (3) and an image to be taken by the at least one camera (3) through reflection in the pair of mirrors (2a, 2b), and wherein a division plane extends through the pair of mirrors and cuts straight through a position where the sample is being imaged by the at least one camera (3), substantially perpendicular to the main axis, where the at least one camera (3) is arranged on a first side of the division plane, and an entirety of the background element (4) is arranged on a second side of the division plane, and the at least one camera (3) is directed obliquely towards the position where the sample is being imaged so that no part of the at least one camera (3) itself is within the field of view of the at least one camera (3) and an image to be taken by the at least one camera (3) through reflection in the pair of mirrors (2a, 2b).

2. The imaging system according to claim 1, wherein the surface of the background element (4) that is directed towards the pair of mirrors is illuminated by at least one background illumination element (5a-c) directed towards this surface.

3. The imaging system according to claim 2, wherein the at least one background illumination element (5a-c) is located outside of the field of view of the at least one camera (3).

4. The imaging system according claim 1, wherein the imaging system is intended for receiving samples (1) with a typical colour and wherein the surface of the background element (4) that is directed towards the pair of mirrors has a colour which is substantially complementary to the typical colour of the samples.

5. The imaging system according to claim 4, wherein the imaging system is intended for receiving seeds (1) and wherein the surface of the background element (4) that is directed towards the pair of mirrors is blue.

6. The imaging system according to claim 1, wherein light is directed towards the respective mirror surfaces of the pair of mirrors from at least one sample illumination element (6a, 6b), where the at least one sample illumination element is arranged above or below the pair of mirrors as seen from the main axis.

7. The imaging system according to claim 1, wherein said background element (4) covers the entire field of view of the at least one camera (3).

* * * * *